United States Patent [19]
Nagamatsu et al.

[11] Patent Number: 6,143,176
[45] Date of Patent: Nov. 7, 2000

[54] METHOD OF CONVERTING ORGANIC WASTES TO VALUABLE RESOURCES

[75] Inventors: Sadasuke Nagamatsu; Tsutomu Higo; Toshio Fukuda, all of Kanagawa-ken, Japan

[73] Assignee: Ebara Corporation, Tokyo, Japan

[21] Appl. No.: 08/845,412

[22] Filed: Apr. 25, 1997

[30] Foreign Application Priority Data

May 1, 1996 [JP] Japan ................................ 8-132568

[51] Int. Cl.$^7$ .................................................. C02F 11/10
[52] U.S. Cl. .................. 210/603; 210/609; 210/631; 210/757; 210/769
[58] Field of Search ..................... 210/603, 609, 210/613, 631, 757, 764, 769, 770

[56] References Cited

U.S. PATENT DOCUMENTS

| | | | |
|---|---|---|---|
| 2,075,224 | 3/1937 | Porteous . | |
| 3,697,417 | 10/1972 | Telezke et al. | 210/609 |
| 3,876,536 | 4/1975 | Pradt et al. | 210/609 |
| 3,930,993 | 1/1976 | Knopp et al. | 210/609 |
| 4,213,857 | 7/1980 | Ishida et al. | 210/603 |
| 4,289,625 | 9/1981 | Tarman et al. | 210/603 |
| 4,318,993 | 3/1982 | Ghosh et al. | 210/603 |
| 4,597,872 | 7/1986 | Andersson et al. | 210/603 |
| 4,657,681 | 4/1987 | Hughes et al. | 210/769 |
| 4,988,442 | 1/1991 | Highsmith et al. | 210/609 |
| 5,188,739 | 2/1993 | Khan et al. | 210/609 |
| 5,264,009 | 11/1993 | Khan | 48/197 |
| 5,451,319 | 9/1995 | Kobayashi | 210/603 |
| 5,635,069 | 6/1997 | Boss et al. | 210/609 |

FOREIGN PATENT DOCUMENTS

| | | |
|---|---|---|
| 0 646 547 A2 | 4/1995 | European Pat. Off. . |
| 2 130 476 | 12/1972 | Germany . |
| 95/14850 | 6/1995 | WIPO . |

OTHER PUBLICATIONS

Michael Klosky et al., "Chlorine, Sulfur, and Soluble Slag Extraction with Energy Density Improvements of a MSW Slurry", Coal Util. Full Syst. The Greening Coal, pp. 205–213, 1994.

Roberto M. Serikawa et al., "Oil Conversion of Vinasse with High–Density Water", Fuel, vol. 71, pp. 283–287, Mar. 1992.

Johannes Christensen, Progess Report on the Economy of Centralized Biogas Plants, Danish Energy Agency, pp. 3–35, Feb. 1995.

Patent Abstracts of Japan, vol. 5, No. 102, Jul. 2, 1981 * abstract *.

*Primary Examiner*—Christopher Upton
*Attorney, Agent, or Firm*—Wenderoth, Lind & Ponack, L.L.P.

[57] ABSTRACT

The improved method of converting organic wastes to valuable resources comprises a methane fermentation step (4) in which a slurry of organic waste is retained for fermentation in an anaerobic digester to thereby generate a methane-containing gas and a fermentation slurry, a hydrothermal treatment step (11) in which the fermentation slurry is subjected to a hydrothermal reaction to thereby generate a carbon slurry, and a concentrating step (14) in which an aqueous phase is separated from the carbon slurry to thereby yield a concentrated carbon slurry having a high heating value. The method is capable of performing an effective hydrothermal treatment on a slurry of low water content, prevents the slurry from putrefaction during retention in the process and it yet is capable of effective treatment of the aqueous phase of the slurry after the hydrothermal treatment.

8 Claims, 1 Drawing Sheet

METHOD OF CONVERTING ORGANIC WASTES TO VALUABLE RESOURCES

BACKGROUND OF THE INVENTION

This invention relates to a method of converting organic wastes to valuable resources. The invention particularly relates to a method by which organic wastes in a solid, sludge or liquid form such as municipal wastes, night soil, sewage sludge and industrial wastes can be converted to valuable resources through a hydrothermal treatment.

Various methods are under development to provide for conversion of wastes into valuable resources through a hydrothermal treatment. According to one proposal, any solid matter in the waste to be treated is ground to particles no greater than several millimeters and a feed slurry is prepared that has a sufficiently high water content to be transported by means of a pump; the slurry is then subjected to a hydrothermal reaction to form a carbon slurry; since the carbon slurry is easily separable from water, it is dewatered and concentrated to have a heating value of at least 4,000–5,000 kcal/kg; the resulting concentrated carbon slurry can be used as a fuel.

The term "carbon slurry" as used herein means a mixture of water and the organic content which has been dehalogenated and deoxigenated in form of $CO_2$ to carbides (called "char"), oils and water-soluble components. The "oils" are substances that are extractable with organic solvents such as dichloromethane. The term "aqueous phase" as used herein means the filtrate obtained by filtering the residue from the extraction with organic solvents. The term "solid phase" as used herein means the remainder that results from the removal of the oils and the aqueous phase. The term "hydrothermal treatment" means an operation in which the feed is pressurized to a level higher than the saturation vapor pressure at the reaction temperature and then heated to the reaction temperature to cause a chemical reaction. In the treatment of wastes such as municipal wastes, the reaction temperature is usually on the order of 300–350° C. and the pressure is about 150 atmospheres.

This method, however, has the following problems. Depending on the waste to be treated, the feed slurry for the hydrothermal reaction may have low fluidity or high viscosity and the water content of the feed slurry must be increased to about 85–90% then, the water processing capacity of the facitity becomes or an unduly great energy load is required in subsequent heating and cooling operations.

In a waste treatment plant, the feed retaining facility usually requires a large enough capacity to absorb the input variations so that a uniform quality of wastes can be supplied to the facility at the subsequent stage. For instance, according to the Guidelines for the Structure of Waste Treatment Plants issued by the Welfare Ministry, it is required that a waste pit in incineration facility should have a capacity equivalent to at least two days of a projected maximal daily retention. As a matter of fact, the waste pit retains a large amount of wastes retains. In a hydrothermal treatment facility, the waste to be treated is desirably transformed to a feed slurry for the hydrothermal reaction and retained in the tank under mixing so as to provide uniformity in the slurry. In fact, however, due to the retention of a large amount of wastes, putrefaction of the slurry progresses to either elevate the COD in the aqueous phase or cause odor and hygienic problems.

After the hydrothermal reaction, the aqueous phase is separated from the carbon slurry and the concentration of the organic matter in the separated aqueous phase becomes significantly lower than that of the organic matter present in the aqueous phase of the feed slurry. Nevertheless, the separated aqueous phase still contains the organic matter at a concentration of $2-3\times10^4$ ppm in the usual case and must be diluted with a large amount of water before it is subjected to a biological treatment. In the case of presence of heavy metals in the aqueous phase, a biological treatment is practically infeasible and a fuel must be employed to perform combustion, or an operation consisting of evaporation and oxidation treatments.

In order to remove the aqueous phase from the carbon slurry that has been subjected to the hydrothermal reaction, dewatering by filtration is performed in the subsequent concentrating step. However, the oils in the slurry will either adhere to the filter surface or clog the filter medium, requiring frequent cleaning of the filter. Therefore, continual operation of the hydrothermal reaction facility not only requires an auxiliary machine for filtration but also imposes a considerable operational load.

Thus, in spite of the substantial progress in the studies on the hydrothermal reaction perse, there have been many problems to solve before the technology for converting wastes into valuable resources in the form of a concentrated carbon slurry of high heating value by a hydrothermal reaction treatment can be implemented as a commercial process.

SUMMARY OF THE INVENTION

An object, therefore, of the present invention is to provide a method for converting organic wastes into valuable resources, which is capable of performing an effective hydrothermal treatment on a slurry of low water content, which prevents the slurry from putrefying during retention in the process, and which yet is capable of effective treatment of the aqueous phase of the slurry after the hydrothermal treatment.

The stated object of the invention can be attained by a method comprising:

a methane fermentation step in which a slurry of organic waste is retained for fermentation in an anaerobic digester to thereby generate a methane-containing gas and a fermentation slurry;

a hydrothermal treatment step in which said fermentation slurry is subjected to a hydrothermal reaction to thereby generate a carbon slurry; and a concentrating step in which an aqueous phase is separated from said carbon slurry to thereby yield a concentrated carbon slurry having a high heating value.

DETAILED DESCRIPTION OF THE INVENTION

Figure 1:
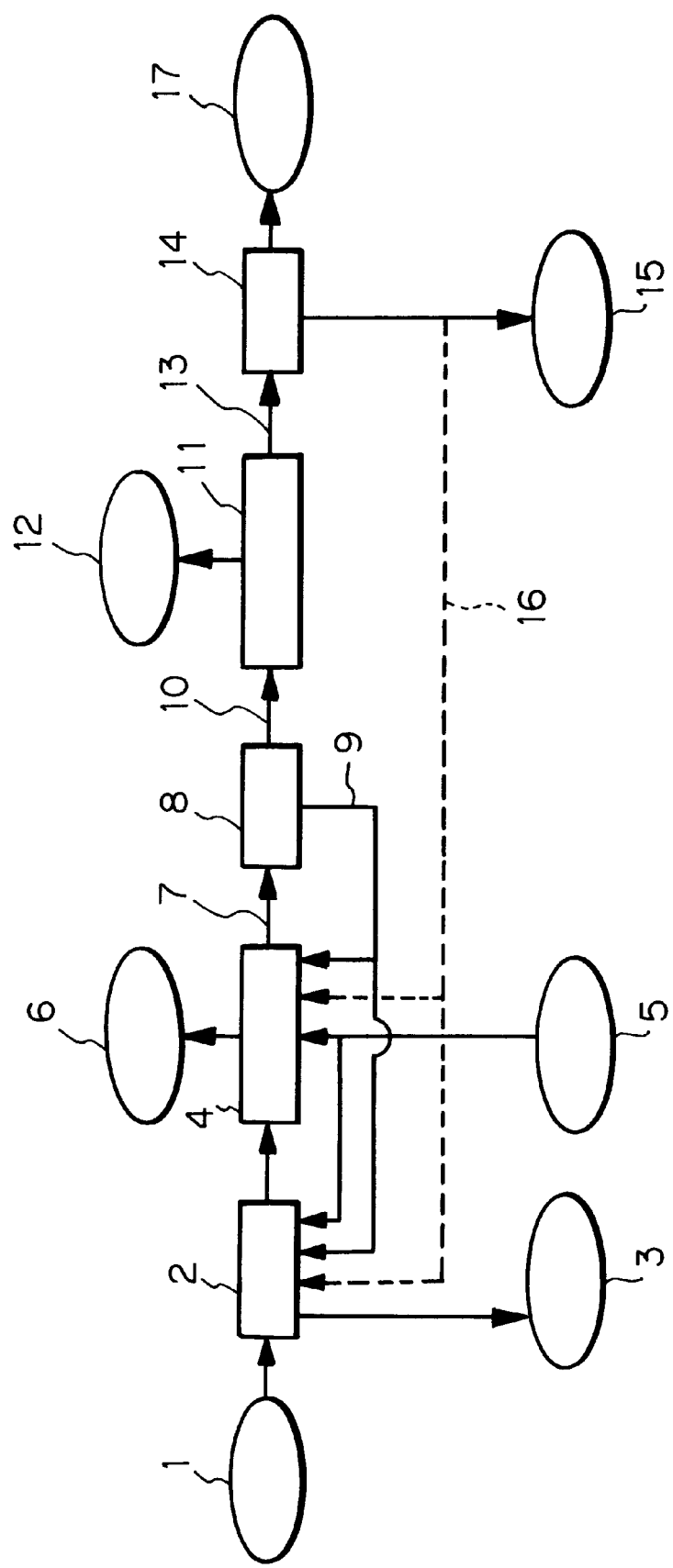
FIG. 1 shows schematically the method of the invention for converting wastes into valuable resources.

The method of the invention will now be described with reference to the accompanying FIG. 1.

FIG. 1 is a flowsheet showing schematically the method of the invention for converting wastes into valuable resources. First, a feed waste 1 is subjected to a preliminary treatment step 2 for removing coarse solids and the like. In this step 2, the solids in the waste are finely ground to particles of less than a few millimeters and the inorganic foreign matter such as glass, tiles pebbles and metals should also be removed as much as possible. If the waste is substantially free of solids or if the solids in it are initially so small as in the case of a sludge or liquid wastes that they do not have to be ground, it is optionally passed through a screen to reject coarse solids larger than about 10 mm as foreign matter 3. A waste slurry can easily be obtained by suspending the waste in a liquid and performing the grinding and separating operations. Alternatively, the waste slurry may be obtained by first grinding and separating the waste and then mixing the residue with a liquid. Another way to make the waste slurry is to add water to the waste in the next step of methane fermentation.

The preliminary treatment step 2 is followed by a methane fermentation step 4, in which either the waste or waste slurry that result from the preliminary treatment is supplied into an anaerobic digester from an end of the bottom, retained in the digester under an anerobic condition, maintained in a neutral range of pH 6–8, held at a temperature of about 30–60° C., and so adjusted that the water-soluble organic matter in the liquid in the middle to the top part of the digester has a COD level of about 5,000–100,000 mg/L. This adjustment is accomplished by addition of makeup water 5. In the digester, the methanogenic cells which adhere to the bubbles of carbon dioxide and methane gases float to the top of the liquid, release the gases and settle to the bottom, thereby imparting a suitable degree of agitation to the middle and the top part of the digester. The digester is of a closed vessel type with the liquid level substantially constant and the methane-rich fermentation gas 6 collecting in the overhead is recovered.

The makeup water 5 is used to adjust the water content of the waste slurry to a level appropriate for methane fermentation. If a submerged grinder such as a pulper is to be used in grinding the waste in the preliminary treatment step 2 or if a gravity separator or a liquid cyclone is to be used in separating the foreign matter, a greater operating efficiency is secured by reducing the solids content in the waste. To this end, the makeup water 5 may be supplied in the preliminary treatment step 2 or, alternatively, it may be supplied to the waste 1 at the retention stage preceding the preliminary treatment step 2. In practice, the water content of the waste slurry is adjusted in the preliminary treatment step 2 to the same level as the water content to be established in the methane fermentation step 4 or, alternatively, the preliminary treatment is effected with a higher water content than in the methane fermentation step and the waste is dewatered after the preliminary treatment, with the resulting water being returned to the preliminary treatment step 2 for further use.

In place of or together with the makeup water 5, the circulating water 9 from the dewatering step 8 after methane fermentation or the circulating water 16 from the concentrating step 14 to be described below may be returned to the preliminary treatment step 2 or the methane fermentation step 4. This is effective in saving the makeup water 5 or reducing the effluent 15 to be discharged from the system.

The methanogenic cells circulate mainly from the middle to the top portion of the digester and vice versa and, hence, those cells that multiply at the slower speed will flow out of the digester in a limited amount if the fermentation slurry 7 is withdrawn from the bottom of the digester at an end opposite to the supply point. A certain kind of wastes has a smaller specific gravity than the liquid in the digester and hence will float to the top. If the entrance of such waste is anticipated, it is recommended to use a mechanism that gently agitates the top surface of the liquid, that causes the methanogenic cell growths on the bubbles to settle to the bottom and that scrapes the floating waste; the waste thusly discharged from the digester may be combined with the fermentation slurry withdrawn from the bottom of the digester. It should be noted here that the digester should not contain toxic substances at high enough concentrations to interfere with methane fermentation; as guide figures, the content of ammoniacal nitrogen should be kept below 200 mg/L and that of sulfur as hydrogen sulfide should be kept below 100 mg/L. Thus, keeping the toxicants at practically acceptable low levels is another reason for adjusting the supply of makeup water.

In the methane fermentation, the water-soluble organic matter is selectively consumed so that the viscous substances will disappear lowering the viscosity of the waste slurry to a level close to that of ordinary water. In this regard, the methane fermentation is significantly effective in modifying wastes that contain large amounts of starches, proteins and microbial cells. The progress of methane fermentation is not substantial in fine particles of the waste that do not dissolve in water. However, easily degradable organic matter such as garbage will undergo progressive putrefaction and will decompose during the hydrothermal treatment in the next step into a form that functions as a slurry lubricant in a most easy way.

The fermentation slurry 7 withdrawn from the digester is sent to the hydrothermal treatment step 11 but prior to that step, the slurry is preferably subjected to the dewatering step 8 to prepare a feed slurry 10 for the hydrothermal treatment. As already mentioned, the water separated from the slurry may be returned as the fermentation circulating water 9 into the digester in the methane fermentation step 4. If the water content of the feed slurry 10 is minimized by this dewatering step, the size of the pumps, heat exchangers and reaction vessel in the hydrothermal treatment system can be reduced and the thermal load required for heating and cooling operations are also reduced. Needless to say, the slurry must be kept sufficiently flowable to be passable as a fluid through the pump and pipes.

The appropriate water content varies with the type of waste to be treated. In wastes rich in food refuse, the solids, that remain undigested, work as a lubricant which imparts fluidity to the slurry and, hence, the amount of free water can be reduced to an extremely low level and it is practicably feasible to prepare a slurry having a water content of about 40%.

The dewatered feed slurry 10 is subjected to the hydrothermal treatment step 11, in which it is exposed to high temperature at high pressure. In a hydrothermal reaction, the temperature is typically at 250–350° C. and the pressure is usually at 50–200 atmospheres, which should be higher than the saturation vapor pressure at a given temperature. The reaction time decreases with increasing temperature and it ranges typically from ten-odd minutes to one or two hours. A reaction in which halogens and oxygen leave the compounds in the feed slurry will start to occur at a tempeature of about 250° C. An oxidizing atmosphere does not favor this reaction but in the absence of deliberate oxygen blowing, a strong reducing condition prevails to permit the progress of deoxygenation and dehalogenation.

As a result of this hydrothermal treatment, the chain structure of the molecule is broken and an emission 12 that is chiefly composed of carbon dioxide gas with small amounts of hydrogen sulfide, mercaptan, ammonia, etc. is discharged. The carbon slurry 13 emerging from the hydrothermal treatment step 11 is a mixture of a solid phase which is a brittle char of high carbon content, oils, and an aqueous phase having water-soluble organic compounds (e.g. lower organic acids, alcohols, aldehyde and ketone) and salts dissolved therein. The content of oils in the carbon slurry 13 is small since the feed slurry 10 obtained by methane fermentation already has the hydrogen content reduced due to methane formation from the starting waste. In addition, the amount of organic compounds in the aqueous phase of the carbon slurry 13 is also small since the amount of the water-soluble organic matter in the feed slurry 10 has decreased selectively due to the methane fermentation. The oils in the carbon slurry 13 are usually tar- or pitch-like heavy oils at ordinary temperature and their pour point typically exceeds 50° C.

As a result of the deoxygenation reaction, the viscosity of the aqueous phase becomes almost equal to that of water and, in addition, the solid phase and the oils are highly settlable and do not form colloids; hence, the carbon slurry 13 can be dewatered efficiently.

The carbon slurry 13 emerging from the hydrothermal treatment step 11 is sent to the concentrating step 14, where it is freed of the aqueous phase to become a concentrated carbon slurry 17 that has a lower water content and, hence, an increased heating value. Depending on the type of waste to be treated, the carbon slurry fed into the concentrating step 14 contains a char and oils that have lower specific gravities than the aqueous phase and, therefore, dewatering by filtration is a common practice in the concentrating step. To this end, the carbon slurry 13 has to be cooled to the lowest possible temperature below 50° C. to convert the oils to a solid form before it is concentrated by dewatering. If cooling is done during the process of concentration such that the oils turn from a liquid to a solid state, the oils will adhere to the concentrator (i.e., filter) to clog the voids and the surface of the filter, as well as upset the balance of the fast moving rotor. The aqueous phase separated in the concentration step 14 has the COD level considerably reduced compared with the feed slurry which is yet to be subjected to methane fermentation (COD=several tens of thousand mg/L); however, the COD level of this aqueous phase is still high. Therefore, it is preferably returned as hydrothermal reaction circulating water 16 back to the digester for methane fermentation to thereby reduce the volume of makeup water 5 to be supplied to the digester and that of the effluent 15 to be discharged from the system. It should, however, be noted that the quantity of the circulating water to be returned to the digester must be such that the concentrations of toxic substances to methane fermentation such as ammoniacal nitrogen and sulfur as hydrogen sulfide will not be high enough to interfere with the methane fermentation.

The following example is provided for the purpose of further illustrating the present invention but is in no way to be taken as limiting.

EXAMPLE

Municipal wastes were slurried and subjected to two experiments; in one experiment, the waste slurry was subjected to both methane fermentation and a hydrothermal reaction; in the other experiment, the slurry was subjected to only a hydrothermal treatment.

The starting municipal wastes consisted of three components, 40% water, 52% inflammables and 8% ash, with the inflammables consisting of 48% C, 8% H, 42% O, 1.0% Cl, 0.6% N and 0.4% S.

The municipal wastes of this composition were freed of the ash content as much as possible and, after the addition of water, the waste was ground with a mixer to particles not larger than a few millimeters; upon addition of methanogenic cells, the slurry was left to stand at a pH of 7–8 for 10 days at a temperature of 34–38° C. Methane and carbon dioxide gases evolved in respective amounts of 89 g and 105 g per kilogram of the waste. The concentration of methane relative to the sum of methane and carbon dioxide was 70 vol %.

The resulting slurry was filtered by standing on filter paper and analysis showed that it consisted of 54% water, 44% inflammables and 2% ash, with the inflammables consisting of 47% C, 5% H, 44% O, 1.5% Cl, 0.9% N and 0.6% S.

This feed slurry that had been subjected to methane fermentation and the other feed slurry which was not subjected to methane fermentation were each subjected to a hydrothermal treatment in an autoclave at a temperature of 325° C. for a reaction period of 10 minutes at a pressure of 150 atmospheres.

The carbon slurry resulting from the hydrothermal treatment of the feed slurry that had not been subjected to methane fermentation consisted of 28% oils, 13% gases, 47% solid phase and 12% soluble matter in the aqueous phase. In contrast, the carbon slurry resulting from the hydrothermal treatment of the feed slurry that had been subjected to methane fermentation consisted of 19% oils, 9% gases, 68% solid phase and 4% soluble matter in the aqueous phase.

The hydrothermal treatment accepts various types of organic wastes ranging from municipal wastes through night soil to industrial wastes and does not require any strict sorting irrespective of whether the waste to be treated is in a solid, sludge, liquid or any other form and yet concentrated carbon slurries of high heating values can be produced. The concentrated carbon slurries can be directly used as fuels for fluidized-bed boilers or they may be converted to CWM for use as a fuel in combustion with burners or, alternatively, they may be used as a starting material for the synthesis of ammonia by the Texaco process. Thus, according to the present invention, organic, wastes can be converted to valuable resources having a wide scope of applicability.

In particular, the feed slurry to the hydrothermal treatment is subjected to decomposition by methane fermentation as a preliminary step and this offers the following advantages:

(1) methane is obtained in a sufficiently high concentration to be useful as a fuel or chemical reagent;

(2) the viscosity and the water content of the feed slurry can be sufficiently reduced to permit the use of compact equipment in the hydrothermal treatment and the separation of the aqueous phase from the hydrothermal reaction product, thereby achieving a significant cutback on the investment and operating costs;

(3) in a waste treatment plant of the type contemplated by the invention, retention of the received waste and its homogenization are two essential steps and this requirement is met by the anaerobic digester which is used as a methane fermenter in the present invention;

(4) the content of the organic matter in the aqueous phase which is separated from the carbon slurry after the hydrothermal treatment is so much reduced that the subsequent treatment of the effluent can be performed easily;

(5) the oils generated in the slurry by the hydrothermal reaction will adhere to or clog the voids in a filter that is used to dewater the slurry to produce a concentrated carbon slurry from which the aqueous phase has been separated; however, according to the invention, the content of such oils is reduced by decomposition through methane fermentation.

Stated briefly, the present invention offers a new technology of converting organic wastes into valuable resources which is characterized by the application of an efficient combination of the recovery of the methane gas which is produced by methane fermentation and the recovery of the carbon slurry which results from the hydrothermal reaction. Thus, the present invention makes great contribution to the art of converting wastes to valuable resources.

What is claimed is:

1. A method of converting organic waste into valuable resources, which comprises:

(a) a methane fermentation step in which a slurry of organic waste is retained in an anaerobic digester to generate a methane-containing gas and a fermentation slurry;

(b) A hydrothermal treatment step in which said fermentation slurry is maintained at a high temperature of from about 250° C. to about 350° C., at a high pressure of from about 50 to about 200 atmospheres, which is higher than a saturation pressure at the high temperature, for 10 minutes to 2 hours, to conduct a hydrothermal reaction to generate a carbon slurry containing a solid phase which consists of char having a high carbon content, oils and an aqueous phase including water soluble organic compounds; and (c) a concentration step in which said carbon slurry yields a concentrated carbon slurry having a high heat value by separating the aqueous phase which is returned to said anaerobic digester.

2. The method according to claim 1, wherein said slurry of organic waste is freed of coarse solid matter before it is subjected to said methane fermentation step.

3. The method according to claim 1, wherein water is added to said organic waste in said methane fermentation step to thereby form a slurry of said waste and maintain the conditions for fermentation.

4. The method according to claim 1, wherein said fermentation slurry is subjected to a dewatering step in order to reduce the water content of said slurry before it is subjected to said hydrothermal reaction.

5. The method according to claim 4, wherein the liquid separated in said dewatering step is returned to said anaerobic digester.

6. The method according to claim 1, wherein the concentrated carbon slurry has a heating value of at least 4,000 kilocalories per kilogram.

7. The method according to claim 1 further comprising the cooling step, prior to the concentration step, in which the carbon slurry is cooled to temperatures less than 50° C.

8. The method according to claim 1 wherein the concentration step comprises filtration.

* * * * *